United States Patent [19]

Zine, Jr.

[11] 4,189,382

[45] Feb. 19, 1980

[54] BLOOD COAGULATION AND SEPARATION

[75] Inventor: Anthony R. Zine, Jr., Corning, N.Y.

[73] Assignee: Sherwood Medical Industries Inc., St. Louis, Mo.

[21] Appl. No.: 892,992

[22] Filed: Apr. 3, 1978

Related U.S. Application Data

[63] Continuation of Ser. No. 521,740, Nov. 7, 1974, abandoned.

[51] Int. Cl.$^2$ ............................................. B01D 21/26
[52] U.S. Cl. ...................................... 210/46; 210/51; 210/59; 210/83; 210/209; 210/DIG. 23
[58] Field of Search .............. 210/46, 51, 59, 83, 210/84, 209, DIG. 23, 516-518; 128/214 R, 272; 23/230 B

[56] References Cited

U.S. PATENT DOCUMENTS

| 2,682,268 | 6/1954 | Ryan et al. ................. 210/DIG. 23 |
| 2,812,231 | 11/1957 | Zar ..................................... 128/272 X |
| 3,492,396 | 1/1970 | Dalton et al. ............... 128/214 R X |
| 3,780,935 | 12/1973 | Lukacs et al. ............. 210/DIG. 23 |
| 3,814,248 | 6/1974 | Lawhead ..................... 210/DIG. 23 |
| 4,052,010 | 10/1977 | Baker et al. ..................... 23/230 B X |

OTHER PUBLICATIONS

Sarstedt-Catalogue 73, Walter Sarstedt, Inc., Princeton, N.J., pp. 1, 6, 7, 10, 30 & 31, (6/15/73).
Catalogue, B-D Standard and Special Formula Vacutainer Tubes, Becton-Dickinson, Rutherford, N.J., p. 18 (1973).
Margolis, "The Effect of Colloidal Silica on Blood Coagulation", Aust. J. Exp. Biol., 39, pp. 249-258 (1961).
J. Margolis, J. Physiol. (1957) 137, pp. 95-109, "Intiation of Blood Coagulation by Glass and Related Surfaces".
Ratnoff et al., American Journal of Medicine, Aug. 1958, pp. 160-168, "Role of Hageman Factor in the Initiation of Clotting by Glass".
Soulier et al., Brit. J. Haemat., 1960, 6, 88, "New Data on Hageman Factor and and Plasma Thromboplastin Antecedent".

Primary Examiner—Robert H. Spitzer
Attorney, Agent, or Firm—Stanley N. Garber

[57] ABSTRACT

Methods and apparatus for separating blood which utilize suspendable contact-activating particles to initiate blood clotting generally throughout the volume of blood are disclosed herein. The contact-activating particles are deposited in a vessel; and when whole blood is supplied to the vessel, the particles are suspended throughout the volume of the blood and remain so suspended, without mechanical agitation, during at least the initial stages of coagulation. The particles are precipitated from the serum portion of the blood during a subsequent centrifugal separation. Also, a process for making appropriately sized contact-activating particles is disclosed.

15 Claims, 4 Drawing Figures

BLOOD COAGULATION AND SEPARATION

This is a continuation, of application Ser. No. 521,740, filed Nov. 7, 1974, now abandoned.

BACKGROUND OF THE INVENTION

1. Field of the Invention

This invention relates to methods and apparatus for separating blood and to processes for producing contact-activating agents adapted to activate clotting factors in blood. More specifically this invention relates to methods and apparatus for separating blood which utilize powdered contact-activating agents to activate blood clotting and to processes for making powdered contact-activating agents.

2. Prior Art

It is well known that the in vitro coagulation of human blood involves a series of enzymatic activation processes and that these processes are enhanced by contacting blood against certain foreign surfaces, especially silicaceous substances, such as glass, kaolin, bentonite, hydrated aluminum silicate and diatomaceous silica or Kieselguhr. A study of the role of surface contact with these materials was published in 1960 the British Journal of Haematology, volume 6, pages 88 through 101, in an article by J. P. Soulier and O. Prou-Wartelle entitled, "New Data on Hageman Factor and Plasma Thromboplastin: The Role of 'Contact' in the Initial Phase of Blood Coagulation".

Blood separation practices have long utilized the clot activation properties of glass insofar as glass tubes have been used to collect and separate blood. The standard method for separating blood has been, first, to deposit a predetermined quantity of blood into a glass tube; second, activating the clotting factors within the blood at the inner surface of the tube; third, without agitation, permitting the activated clotting factors to diffuse or migrate toward the center of the tube; fourth, maintaining the clotting process to obtain substantially complete coagulation; and fifth, centrifugally separating the coagulated blood into a lighter phase consisting essentially of serum and a heavier phase consisting essentially of cellular and fibrillar matter.

In order to assure substantially complete coagulation, this standard method normally involves a lengthy waiting period between the collection or deposition of the blood into the tube and the centrifugal separation of the blood. In fact this waiting period is no less than 30 minutes and may last as long as 100 minutes, the length of time being dependent upon the clotting characteristics of the particular blood sample. It has been theorized that the clotting time is dependent on the total surface area of the glass and the duration of time that the blood is in contact with the surface area. I have found that the clotting time is also dependent upon the rate of diffusion or migration of the activated clotting factor from the activation sites, that is, at the inner surface of the conventional blood separation vessel to the center of the vessel.

Thus a major problem associated with the standard blood separation methods and practices is the lengthy waiting period needed to assure substantially complete coagulation before separation. It is an object of this invention to provide a method and apparatus for separating blood which substantially reduces this waiting period.

Another problem associated with the standard blood separation methods and practices relates to the latent formation of fibrin in the lighter or serum portion of the separated blood. The blood coagulation process includes the conversion of fibrinogen to fibrin, fibrin being the fibrillar structure within which cellular material (red cells, white cells, platelets, debris, etc.) are entrapped to form a clot. In the event that a blood sample is centrifugally separated before coagulation is substantially complete, the lighter or serum portion will contain fibrinogen and activation agents which will react in the separated lighter portion to form fibrin strands. Inasmuch as the testing devices used to analyze the serum portion include intricate plumbing systems, it is essential that the serum portion be free from fibrin contamination. Also, it should be noted that even minute amounts of fibrin contamination of the serum might affect the apparent chemistries of the serum measured by the testing devices, should the amount of fibrin be so minute as to pass through the testing device without obstructing the passageways therein.

Accordingly, another object of this invention is to provide methods and apparatus which will eliminate the problem of latent fibrin formation within the lighter or serum portion of a separated blood sample.

Another problem associated with standard blood separation devices and methods pertains to the relative cleanliness of the lower portion of the serum or lighter portion of separated blood. After complete coagulation, the clot of cellular and fibrillar matter extends throughout the volume of the coagulated blood. Upon centrifugation, due to the higher specific gravity of the cellular portion of the blood, the cellular matter is sedimented under the influence of the applied centrifugal force, and the fibrillar matter is drawn with the cellular matter out of the lighter portion. Fibrillar strands in the upper portion of the pre-centrifuged blood may be unattached to cellular portions; in this event, these strands may remain suspended in the serum portion after centrifugation. Also, such strands may be free from red cells but attached to the fibrin network of the precentrifuged clot, in which event such strands may, after centrifugation, remain attached to the clotted material but remain suspended above the bulk of the heavier portion of the separated sample. Thus, a fibrin or "white layer" may appear at the interface between separated portions of the blood. In order to avoid contamination of the serum with this matter, less serum may be aspirated from the separated blood than actually is available in the lighter portion of the blood.

Accordingly it is another object of this invention to provide an apparatus and method for separating blood which eliminates this problem of fibrin contamination. More specifically, it is an object of this invention to eliminate fibrin contamination caused by either latent conversion of fibrinogen into fibrin after centrifugation or by the suspension within the serum portion of fibrin formed before centrifugation.

It is another important object of this invention to provide methods and apparatus for separating blood which permit the utilization of separation vessels made from materials which are durable, safe, convenient to use, inexpensive and easy to manufacture in any form, and yet which would not require skills or manipulations in excess of those required for standard blood separation procedures. The standard vessel used in separating blood is made from glass; and coagulation is accomplished without agitation, with the inner surface of the glass being the only surface used to activate the clotting factors. The present invention provides for a method of activating the clotting factors at surfaces other than those of the vessel and thus permits the utilization of vessels made from plastic, metal and other materials, without additional manipulative steps beyond those required under conventional procedures for blood separation.

A more recently developed method for separating blood utilizes glass or kaolin granules within a plastic tube. In this method, the granules are deposited in the tube, blood is supplied to the tube, and the tube is agitated by a mixing device. In addition to the activation of clotting factors at the inner surface of the tube, activation also takes place at the surfaces of the granules.

However, this method requires mechanical agitation immediately after the collection of the blood and throughout at least the initial stages of coagulation of the blood. Without such mechanical stirring, the granules would remain in their initial positions within the filled tube, generally adjacent the tube wall and thus would activate only the peripheral bottom portions of the blood within the tube.

Accordingly, it is another important object of this invention to provide apparatus and methods for separating blood which do not require agitation of the blood to be separated.

SUMMARY OF THE INVENTION

This invention provides for new and improved methods and apparatus for separating blood and for a process of manufacturing contact-activating particles. The apparatus comprises a vessel and a preselected amount of contact-activating powder or particles of a size and density adapted to remain suspended generally throughout a volume of blood contained within the vessel during at least the initial stages of coagulation of the blood and to completely separate from the serum portion of the blood during centrifugal separation of the blood, thus permitting rapid activation of clotting factors throughout the volume of blood without agitation and assuring that the separated serum portion is free from contamination by fibrin and the contact-activating particles.

The apparatus may also include a preselected volume of separating gel and an energizer member, the gel being initially positioned at the closed end of the vessel and the energizer member being partially submerged in the gel. The contact-activating material may be applied to an interior surface of the energizer member.

The method of the present invention includes the following steps: providing a vessel with a preselected amount of contact-activating particles; supplying the vessel with a body of blood and simultaneously suspending a substantial portion of the contact-activating particles generally uniformly throughout the body of blood; activating clotting factors within the blood generally uniformly throughout the body of the blood concurrently at the inner surface of the vessel and at the surfaces of said suspended contact-activating particles; maintaining said activation throughout the body of blood to substantially complete coagulation of the blood; and centrifuging the body of blood to separate the blood into a lighter phase consisting essentially of serum and a heavier phase consisting essentially of cellular and fibrillar matter and the contact-activating particles.

The method may also include the step of, after providing the vessel with a preselected amount of contact-activating particles, evacuating and sealing the open end of the vessel with a needle-pierceable closure means.

The process of forming the material of the present invention includes the steps of: finely dividing contact-activating material having a density greater than that of serum; suspending such finely divided material in a suspending medium having a density not greater than that of blood, such as water; sedimenting from the suspension some of the finely divided material under the influence of one gravity (G) of gravitational force; separating the sedimented material from the remaining suspension; under the influence of a centrifugal field similar to that used to separate coagulated blood, precipitating from suspension the finely divided material not sedimented from suspension under one gravity of force; separating the precipitated material from the remaining mixture; and, drying the finely divided material precipitated from suspension under the influence of said centrifugal field.

The present invention also provides for a new and improved apparatus comprising, in combination a vessel adapted to contain blood during coagulation and separation and a preselected quantity of finely divided contact-activating powder manufactured according to the process described above.

DESCRIPTION OF THE PREFERRED EMBODIMENTS

Figure 1:
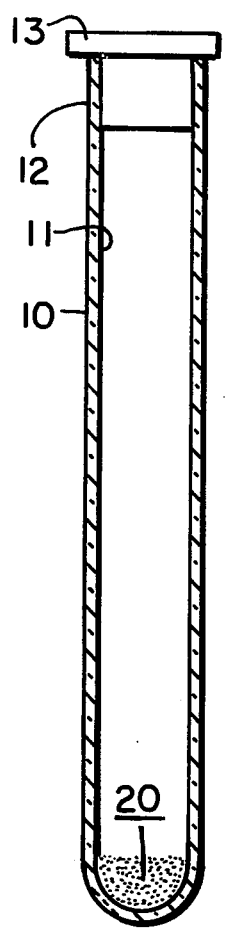
FIG. 1 depicts an embodiment of the apparatus of this invention comprising a closured vessel, which may be evacuated, having a preselected amount of contact-activating particles positioned at the bottom of the vessel.

One preferred embodiment of the apparatus of the present invention is illustrated in FIG. 1, and comprises a vessel 10 having an open end 12 through which blood may be supplied, a closure means 13 for sealing end 12, and clot-promoting or contact-activating powder or particles 20 initially deposited in vessel 10.

Vessel 10 may be composed of glass, plastic, or any other material which is chemically inert, that is, non-interactive with the blood to be separated, and sufficiently durable to withstand the forces exerted during centrifugal separation of blood. Also, the vessel may be composed of material or materials capable of holding a vacuum for a long period and may have a vacuum-tight, needle-pierceable closure means 13; such a vessel could be used to collect blood by means of siphoning, as is disclosed in U.S. Pat. No. 2,460,641 to Kleiner. It is not necessary that the vessel material itself be capable of activating clotting factors within blood. However, glass such as Corning Glass Works Code No. 7740 borosilicate glass, also known under its registered trademark, PYREX®, is particularly suitable material for vessel 10 because it is not only durable and chemically inert but also provides an excellent adsorbent inner surface 11 for activating blood clotting factors. Also, a glass vessel is capable of holding a vacuum for purposes of drawing blood upon venipuncture and is pleasing in its appearance.

Contact-activating particles 20 are composed of materials which serve to activate clotting factors of whole blood, such materials including, for example, glass, kaolin, bentonite (hydrated aluminum silicate), and diatomaceous silica. With regard to the types of glass, it has been found that borosilicate glass, having a density ranging from 2.16 to 2.43 grams per cubic centimeter, and particularly Corning Code 7740, sold under the trademark, PYREX®, is an excellent clot activating material.

Particles 20 are of a density and sufficiently small size to be generally uniformly dispersed or suspended throughout the total volume of blood as blood is siphoned or poured into container 10 and to remain suspended during at least the initial stages of coagulation of the blood, and yet to be sedimented from the light or serum portion of separated blood during the centrifugal separation of the blood.

Particles 20 are made from material having a specific gravity or density higher than the serum portion of the blood to be separated, are of a sufficiently small size to remain suspended or dispersed throughout the total whole blood volume under the influence of 1 G of gravitational force without the necessity for the expenditure of mechanical work on the mixture, but are large enough and of a density to be sedimented from the serum portion during the centrifugal separation of the blood. In other words, the clot-activating particles are of a size and weight to achieve a substantially stabilized suspension in whole blood under 1 G of gravitational force and to sediment from the serum portion during the centrifugal separation of the blood.

The finely divided or particulate contact-activating agent 20 of the present invention completely eliminates any worry concerning contamination of the separated serum portion with the contact-activating agent. The minimum particle size of activating powder 20 is preselected to eliminate the possibility that smaller particles will remain suspended in the serum throughout centrifugation at the normal magnitude of the centrifugal force (for example, up to 1100 G's) and for the normal period (for example, up to 15 minutes). If the minimum particle size was not so preselected, even though the density of the particles is higher than that of the serum, the smaller particles of the powder could be colloidally or semicolloidally suspended in the serum to the extent that an increased centrifugal force or a longer centrifugation time would be required to precipitate such smaller particles. Such increased force or time is highly undesirable because it may result in hemolysis of the red cells and hence falsely elevated levels of lactic dehydrogenase, potassium or hemoglobin within the separated serum.

The maximum particle size of particle 20 is preferably small enough to remain suspended during at least the initial stages of coagulation that is, for the first two to five minutes of coagulation. However, it is only necessary that the contact-activating agent be in the form of a finely divided powder. Some of the advantages achieved by a powder are, first, that a powder does not sediment rapidly in blood but tends to remain suspended throughout a volume of blood and thus provides for a greater duration of surface activation in those areas of the blood separated from the vessel walls; second, a given weight of finely divided powder has greater surface area than an equal weight of granules or spheres and thus provides a greater contact surface area for activation of clotting factors; and, third, due to the relatively low total mass of a particle of powder, precipitation of powder during centrifugation is less likely to collide against red cells with enough force or momentum to cause hemolysis or rupturing of the red cells and thus provides for a separated serum that is free from falsely elevated amounts of lactic dehydrogenase, potassium and hemoglobin. Due to the fact that powder sediments slowly in blood, mechanical agitation of the mixture is not necessary. Thus, it will be appreciated that a contact-activating coagulation agent in the form of a powder having a density greater than the serum phase and a minimum particle size capable of being precipitated during the centrifugal separation of blood not only reduces coagulation time due to the increased contact surface area and the increased duration of time that the aid is in contact with the nonperipheral portions of the blood, but such a powdered aid eliminates the need for mechanical agitation and the risk of hemolysis associated with the collision of the coagulation agent and the red cells.

This invention also provides for a process of making particles of a size and density applicable for use as a self-suspendable blood coagulation aid comprising the following steps: first, a clot-activating material having a density greater than that of the serum phase of blood is ground to produce a finely divided powder; second, the finely divided powder is mixed with a suspending medium having a density not greater than that of blood such as water, to suspend at least some of the powder in the medium; third, larger heavier particles suspended in the medium are sedimented under the influence of 1G of gravitational force and separated from the remainder of the mixture; fourth, substantially all of the mixture other than the sedimented heavier particles is subjected to a centrifugal field of a force approximating the applied to separate serum from coagulated whole blood; and fifth, the fraction centrifuged from the centrifuged mixture is separated and dried.

By way of example, Corning Code 7740 glass, having a density of about 2.23 grams per cubic centimeter, was ball milled and a −325 mesh screen was used to fraction off the larger glass particles. The finely divided glass was then mixed with water and the mixture was allowed to stand for up to five minutes, thus allowing the heavier particles to sediment under the influence of one gravity (G) of gravitational force. The portion of the mixture that had not settled was decanted into another container and was thereafter centrifuged at up to 1100 G's for up to 7 minutes. The fraction centrifuged from the mixture was retained and dried in a vacuum oven at about 100° Centigrade. The particle size obtained by this process ranged from 0.4 microns to 20 microns; and the average particle size was about 4 microns.

This process produces a contact-activating powder having a preselected particle size range. The steps of sedimenting heavier particles from the mixture of the powder and suspending medium and separating the heavier particles from the mixture assures a maximum particle size which is smaller than that which either will remain in the peripheral portion of collected blood, unless the particles and blood are mechanically agitated, or will sediment rapidly into peripheral portions of the collected blood. The step of subjecting the suspension to a centrifugal force approximating that experienced during the centrifugal separation of blood into red cell and serum phases assures that the minimum particle size is capable of being precipitated from the serum phase of blood during the centrifugal separation of blood.

It will be appreciated that the maximum particle size produced by this process is dependent on the method of grinding the contact-activating material into a powder and upon the length of time the larger particles are permitted to sediment from suspension. If the material were to be ground extensively to a very finely divided powder, practically no particles would sediment within the first two to five minutes after being mixed with the suspending medium. Since a powdered contact-activating agent will probably remain suspended in blood after five minutes due to the higher viscosity of the partially coagulated blood, it would not be necessary to subject a mixture of such a very finely divided powder and a suspending medium to the step of sedimenting heavier particles from the mixture.

Also, if the grinding of the contact-activating material were to produce a particle size distribution having an average particle size capable of remaining suspended for five minutes or more in a suspending medium having a density not greater than that of blood, then it again would not be essential to the purpose of this invention to include in the process for making the powdered activator the subsequent step of separating the sedimented larger particles from the remaining mixture of powder and suspending medium.

Of course, the particle size distribution or range of particles 20 is dependent upon the density of the material involved. Since the surface configurations of the particles are not regular geometrical shapes, it is not possible, under current measuring practices, to determine the surface area of the particle and correlatively the frictional force exerted on the particle by the suspending liquid. Thus, it is not possible to mathematically determine a specific range of operable particle sizes because the rate of sedimentation is dependent upon the force of the gravitational or centrifugal field applied and the frictional force exerted by the blood components on the particle surface.

Hence, the apparatus of this invention includes clot-activating particles defined in terms of a size and density suitable for obtaining a generally stabilized suspension in whole uncoagulated blood, and for obtaining precipitation from the serum portion during the centrifugal separation of blood. Also, the apparatus of the present invention may be described as comprising a vessel means and a preselected amount of contact-activating powder having a particle size and density defined in terms of a process by which they may be made.

Figure 4:
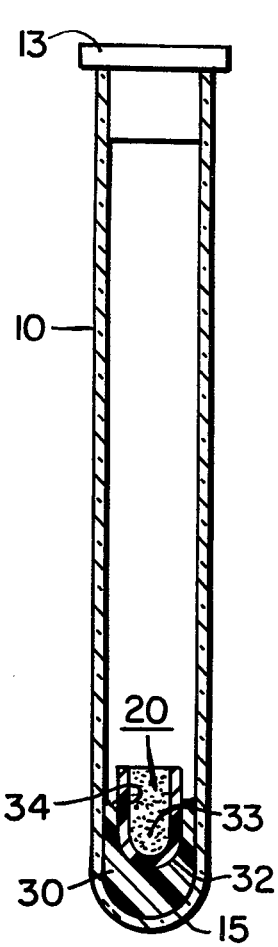
FIG. 4 illustrates another embodiment of the apparatus of this invention comprising a closured and evacuated tube having gel-like material and a plastic energizer member at the bottom thereof and having contact-activating particles deposited generally on the inner surface of the energizer member.

Another preferred embodiment of the apparatus of this invention additionally includes, as shown in FIG. 4, a preselected amount of separating gel 30 preferably initially positioned at the closed lower end of vessel 10 and an energizer means 32 for forcing gel 30 upwardly away from its initial position during the centrifugal separation of blood. Gel 30 may be of the type described in United States Patent application No. 314,270 filed Dec. 11, 1972, now U.S. Pat. No. 3,852,194, and assigned to the assignee of this invention. Gel 30, which may be thixotropic, must be chemically non-interactive with blood or its components and have a specific gravity or density intermediate the specific gravities of the heavier and lighter phases of the blood to be separated. During centrifugal separation of blood, the gel flows from its initial position at one end of the vessel to a second position intermediate the separated blood phases, thereby physically and chemically separating the phases.

The energizer means may be of the type described in United States patent application Ser. No. 452,059 filed Mar. 18, 1974 and assigned to the assignee of this invention, now U.S. Pat. No. 3,920,549. Energizer means 32 may be in the form of a member having an uppermost surface provided with a cavity 33 and a closed lower end. The lower end is submerged in gel 30 and, upon centrifugation, forces the gel away from its position adjacent the closed end 15 of tube 10. Contact-activating particles 20, as described hereinabove, are preferably removably applied to the interior surface 34 of cavity 33 within the uppermost surface of energizer means 32. As blood is supplied to the vessel, particles 20 automatically disperse into suspension generally throughout the volume of the blood and remain so suspended, without mechanical agitation, throughout the coagulation of the blood. Upon application of centrifugal force, particles 20 are precipitated with the heavier phase toward the closed end of the vessel and away from the lighter phase of the blood which is moved toward the open end, and gel 30 rises from the closed end to physically and chemically partition the separated lighter and heavy phases of the blood.

The present invention also provides for an improved method of separating blood into a serum or liquid portion and a heavier portion containing cellular and fibrillar matter. The standard known method of separating blood comprises the following steps: providing a glass tube with a body of blood; activating clotting factors within the blood solely at the inner surface of the tube to activate clotting factors in peripheral portions of the body of blood; permitting the activated clotting factors to diffuse or migrate from near the inner surface of the tube toward the center of the tube to clot the blood between the peripheral portions of the body of blood and the center of the tube; and, centrifuging the body of blood to separate into a heavier phase containing fibrillar and cellular matter and a lighter portion containing serum.

Another known method utilizes granule-sized particles in combination with a plastic tube to coagulate whole blood. This method includes the additional step of continuously mechanically agitating the blood in order to move the granules through the blood. Without agitation, the granules tend to remain in or rapidly sediment into the lowermost portion of the body of blood. Moreover, due to the mass of the granules, the tubes are tilted and rolled at an angle varying slightly from a horizontal position in order to cause the particles to move generally horizontally through the blood. Thus, a special mixer and procedure is required under this known method.

Figure 2:
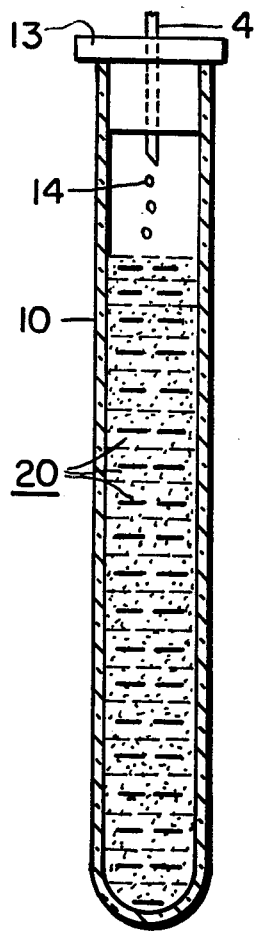
FIG. 2 illustrates the second step of the method of the present invention; it shows blood being supplied to a vessel containing contact-activating particles and, simultaneously, the contact-activating particles being substantially suspended generally throughout the volume of the blood.
Figure 3:
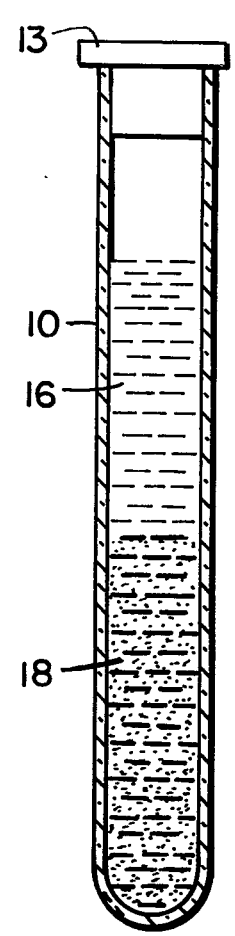
FIG. 3 illustrates the final step of the method of the present invention; the blood is being centrifugally separated into a lighter portion containing serum and a heavier portion containing cellular and fibrillar matter and the contact-activating particles.

The present invention provides for an improvement over these prior methods of separating blood and comprises the following steps:

(a) providing a vessel with a preselected amount of clot-activating particles, as shown in FIG. 1;

(b) supplying the vessel with a body of blood; as depicted in FIG. 2;

(c) suspending a substantial portion of the clot-activating particles generally uniformly throughout the body of blood, simultaneously with the supplying of blood to the vessel, as also depicted in FIG. 2;

(d) activating clotting factors within the blood generally uniformly throughout the body of the blood simultaneously at the inner surface of the vessel and at the surfaces of the suspended clot-activating particles;

(e) maintaining said activation throughout the body of blood to substantially complete the coagulation of the blood; and (f) centrifuging the body of blood to separate the blood into a lighter portion containing serum and a heavier portion containing fibrillar and cellular matter and the clot-activating particles, as shown in FIG. 3.

FIG. 2 depicts the simultaneous steps of supplying the vessel with a body of blood and of suspending the contact-activating particles generally uniformly throughout the body of blood. As shown in this drawing, the vessel may be provided with a pierceable closure means 13 through which blood 14 may be supplied by means of a needle 40. More particularly the needle-pierceable closure 13 may be sealed in the open end 12 of the vessel after the vessel has been evacuated. Accordingly, blood may be siphoned into the vessel by venipuncture with a double-ended needle; and as the blood flows or pours against the contact-activating particles, the particles are automatically dispersed throughout the increasing volume of blood.

Upon the completion of the filling of the tube with blood, the particles are generally uniformly suspended throughout the volume of the uncoagulated blood, thus establishing contact-activation sites throughout the volume of the blood. Coagulation then occurs very rapidly and is substantially complete within 2-15 minutes. The vessel is then centrifuged; and, as shown in FIG. 3, the blood is separated into a lighter phase 16 containing serum (depicted by light dashed lines), and a heavier phase 18 containing cellular and fibrillar matter (depicted by heavy dashed lines) and contact-activating particles 20 (depicted as specks).

This invention also provides for a new and useful improvement in the method described in United States Patent application Ser. No. 452,059 filed Mar. 18, 1974, and assigned to the assignee of the present invention, now U.S. Pat. No. 3,920,549. The method set forth therein for separating blood involves the additional steps of providing a vessel with a quantity of separating gel 30; partially submerging an energizer member 34 into the gel; centrifugally forcing the energizer member into the gel after coagulation of the blood, and moving the gel toward the eventual interface between the lighter and heavier phases of the blood; and continuing the centrifugation until the lighter and heavier phases have separated and the gel has partitioned the phases.

Accordingly, another preferred embodiment of the method of the present invention provides for the following steps in addition to those set forth above:

(1) providing a vessel with a preselected quantity of separating gel and partially submerging an energizer member into the gel;

(2) removably applying contact-activating particles to the energizer member; and (3) after substantially completing the coagulation of the blood, centrifugally forcing the gel to a position between the lighter phase containing serum, and the heavier phase containing cellular and fibrillar matter and the contact-activating particles.

The methods of this invention do not require agitation of the vessel or the positioning of the tube at a horizontal angle to either put the clot-activating particles in suspension or to maintain the particles in suspended positions. The elimination of this agitation step not only results in a much simplified operation but also assures rapid coagulation because the particles are suspended immediately upon collection of the sample. Also, due to the establishment of activation sites throughout the collected blood, fibrinogen is converted to fibrin so rapidly that all of the fibrinogen is converted before centrifugation, thus eliminating the possibility of latent fibrin formation in the separated serum phase.

Also in those methods which utilize granule-sized particles, due to their weight the granules have a tendency to remain aggregated adjacent the inner walls of the vessel. The blood will quickly coagulate in the vicinity of the aggregated granules; and since the blood in the vicinity of granules becomes more viscous as coagulation occurs, it becomes increasingly more difficult to shake the granules out of the viscous coagulated portion and to put the granules into the less viscous uncoagulated portions of the blood. Due to the immediate self-suspending characteristics of particles of this invention, there is no possibility that the particles will become aggregated within peripheral portions of the blood.

Also it should be noted that the present method can be accomplished without the removal of the closure means; that is, from venipuncture and withdrawal of blood from a patient into a vessel and through coagulation and separation of the serum from the blood, the closure means may remain in a sealed position within the opening of the vessel. By maintaining the tube in a closed configuration, the hazard of infection of laboratory personnel is considerably reduced.

It is to be understood that the methods, apparatus and process disclosed herein may be employed in ways and forms different from those of the preferred embodiments without departing from the spirit and scope of the appended claims.

I claim:

1. An improved method of collecting a sample of whole blood within a vessel having a sidewall terminating at first and second ends, coagulating the blood to form intermixed serum and red cell phases, and simultaneously separating said phases and partitioning said phases with a quantity of thixotropic material having a density intermediate the densities of said phases, including the steps of initially positioning the thixotropic material within the vessel adjacent the first end thereof, partially submerging energizer means for directing the flow of said thixotropic material within said thixotropic material, introducing the sample of blood into said vessel through the second end thereof, activating the clotting factors of said blood at inner surface portions of said vessel to form intermixed serum and clotted red cell phases, and applying centrifugal force to said sample of blood, thixotropic material and energizer means to simultaneously separate said phases, move said energizer means into said thixotropic material, and to move said thixotropic material from said first vessel end to a position partitioning said phases, wherein the improvement comprises the steps of:

removably applying to said energizer means a quantity of particles made from material which promotes the clotting of blood, each of said particles having a density and size sufficient to be suspended in said sample of whole blood as said sample is supplied to the vessel and to be sedimented from said serum phase during the application of centrifugal force to separate said sample into said serum and red cell phases;

simultaneously with said step of supplying said sample of blood to said vessel, suspending said particles in said sample, to establish a plurality of sites for the contact activation of clotting of blood throughout said blood sample whereby the time for complete coagulation is substantially reduced; and, concurrently with the step of applying centrifugal force to separate said serum and red cell phases, centrifugally forcing said particles into said red cell phase, whereby said separated serum is free from said powdered means.

2. The improved method of claim 1 further comprising the steps of evacuating said vessel, inserting a needle-pierceable stopper in said second end of said vessel to form a removable sealed relationship therewith, and siphoning blood through said stopper with a needle.

3. A method of collecting blood, coagulating the blood and centrifugally separating the blood into a serum phase and a red cell phase comprising the steps of:

(a) providing a vessel with contact-activating particles, said particles having a density greater than the serum phase of blood and being of a size sufficient to facilitate their initial and continued suspension in a body of blood as said body of blood is supplied to said vessel means and to also facilitate their precipitation from the serum phase of said body of blood during the centrifugal separation of said serum phase from said body of blood;

(b) evacuating the vessel, and sealing an open end of the vessel with a closure;

(c) siphoning blood through the closure to supply the vessel with a body of blood, and simultaneously with such flow of blood initially suspending a substantial portion of the contact-activating particles generally uniformly throughout the body of blood;

(d) activating clotting factors within the blood generally uniformly throughout the body of the blood concurrently at the inner surface of the vessel and at the surfaces of said suspended contact-activating particles;

(e) maintaining in suspension said initially suspended particles throughout the body of blood, and continuing said activation of clotting throughout the body of blood to substantially complete coagulation of the blood, this step being performed substantially without agitating the vessel; and (f) centrifuging the body of blood to separate the blood into a lighter phase consisting essentially of serum and a heavier phase consisting essentially of cellular and fibrillar matter and the contact-activating particles.

4. A method of separating a serum phase from blood comprising the steps of:

providing a vessel with a preselected quantity of gel-like material having a density intermediate the densities of a lighter phase of blood consisting essentially of serum and a heavier phase of blood consisting essentially of cellular and fibrillar matter;

partially submerging an energizer member in the gel-like material;

removably applying a preselected amount of contact-activating particles to the energizer member, said particles having a density greater than said lighter phase of blood and being of a size sufficient to facilitate their initial suspension in a body of blood as the body of blood is supplied to the vessel and to also facilitate their precipitation from said lighter phase during the centrifugal separation of said lighter phase from the body of blood;

supplying the vessel with a body of blood and simultaneously initially suspending a substantial portion of the contact-activating particles generally uniformly throughout the body of blood;

activating clotting factors within the blood generally uniformly throughout the body of the blood concurrently at the inner surface of the vessel and at the surfaces of said suspended contact-activating particles;

continuing to suspend said initially suspended particles and maintaining said activation of clotting throughout the body of blood to substantially complete coagulation of the blood; and after the substantially complete coagulation of the blood, centrifugally forcing the body of blood to separate into a lighter phase consisting essentially of serum and a heavier phase consisting essentially of cellular and fibrillar matter and the contact-activating particles, and centrifugally forcing the gel-like material to a position intermediate the lighter phase consisting essentially of serum and the heavier phase consisting essentially of cellular and fibrillar matter and the contact-activating particles.

5. The method of claim 4 further including the steps of evacuating the vessel, sealing the open end of the vessel with a pierceable closure and supplying the blood to the vessel by siphoning the blood through the closure.

6. A method of separating a serum phase from whole blood comprising the steps of:

providing a vessel with a preselected quantity of gel-like material having a density intermediate the densities of a lighter phase of whole blood consisting essentially of serum and a heavier phase of whole blood consisting essentially of cellular and fibrillar matter;

providing the vessel with means for directing the gel-like material from its initial location toward its position intermediate said lighter phase and said heavier phase during centrifugation of the vessel means;

providing the interior of said vessel with a preselected amount of contact-activating particles, said particles having a density greater than said lighter phase of said whole blood and being of a size sufficient to facilitate their initial suspension in a body of whole blood as the body of blood is supplied to the vessel and to also facilitate their precipitation from said lighter phase during the centrifugal separation of said lighter phase from said body of blood;

supplying the vessel with a body of whole blood and simultaneously initially suspending a substantial portion of said contact-activating particles generally uniformly throughout the body of blood;

activating clotting factors within the blood generally uniformly throughout the body of the blood concurrently at the inner surface of the vessel and at the surfaces of said suspended contact-activating particles;

continuing to suspend said initially suspended particles and maintaining said activation of clotting throughout the body of blood to substantially complete coagulation of the blood; and after the substantially complete coagulation of the blood, centrifugally forcing the body of blood to separate into a lighter phase consisting essentially of serum and a heavier phase consisting essentially of cellular and fibrillar matter and the contact-activating particles, and simultaneously centrifugally forcing the gel-like material to a position intermediate said lighter phase and said heavier phase.

7. The method of claim 6 wherein said means for directing the gel-like material includes a member having a density greater than that of the gel-like material and centrifugally urging the member against the gel-like material facilitating the movement thereof.

8. The method of claim 6 or 7 wherein the step of continuing to suspend said initially suspended particles is performed substantially without agitating the vessel.

9. An apparatus for centrifugally separating blood into serum and clotted red cell phases and for simultaneously partitioning the phases comprising:

partially evacuated vessel means for collecting a sample of fresh blood to be coagulated and thereafter separated into serum and clotted red cell phases under the influence of centrifugal force, said vessel means having first and second ends, with said first end having a needle-pierceable closure inserted therein in an air-tight sealed relationship therewith;

gel-like means for forming a partition between said blood phases simultaneously with their centrifugal separation, said gel-like means being chemically inert with respect to blood and having a density intermediate the serum and clotted red cell phases of blood, and said gel-like means being initially positioned within said second end of said vessel means;

energizer means, initially partially submerged within said gel-like means, for directing the flow of said gel-like means during the centrifugal separation of the phases;

powder means for establishing coagulation activation sites at a plurality of positions dispersed generally throughout the sample of whole blood as the blood is supplied to the vessel means, said powder means being initially removably applied to said energizer means; and, said powder means comprising a plurality of particles of material which promotes coagulation of whole blood, said particles having a density and a selected particle size sufficient to allow the particles to be initially suspended within said sample of blood as said sample is collected within said vessel means and to remain suspended therein during coagulation, and said particles having a density greater than the density of said serum phase and a minimum particle size sufficient to allow all of said particles to be separated from the serum phase of said blood sample into the clotted red cell phase simultaneously with the centrifugal separation of said phases.

10. The apparatus of claim 9 wherein said particles comprising said powder means have a minimum particle size and density which will precipitate from a mixture of said particles with water under the influence of centrifugal force approximating in magnitude the centrifugal force used to separate the serum phase from coagulated blood.

11. The apparatus of claim 10 wherein said particles comprising said powder means will precipitate from a mixture of the particles with water under the influence of centrifugal force of up to 1100 gravities.

12. The apparatus of claim 9 wherein said particles comprising said powder means are made from glass having a density of approximately 2.23 grams per cubic centimeter and have a minimum particle size of approximately 0.4 microns.

13. An apparatus for collecting blood and centrifugally separating the blood into a serum phase and a red cell phase comprising, vessel means for collecting a body of blood; gel-like means for establishing a barrier between the separated serum and red cell phases, said gel-like means being thixotropic in nature and having a density between the densities of the serum and red cell phases; energizer means having a density greater than the density of said gel-like means for initiating and directing the flow of said gel-like means, with said gel-like means being initially positioned adjacent one end of said vessel means and said energizer means being initially partially submerged in said gel-like means; and powdered means within said vessel means for establishing blood clotting contact-activation sites throughout said body of collected blood, said powdered means comprising a plurality of particles made from a clot promoting material, each particle having a density greater than that of said serum phase and a size sufficient to allow both initial and extended suspension thereof within said body of blood as said body of blood is supplied to said vessel means, with said particles having a minimum particle size capable of being precipitated from said serum phase during centrifugal separation of said blood into said phases, whereby the establishment of activation sites throughout the blood assures complete coagulation before centrifugal separation and said minimum particle size assures complete precipitation of said powdered means during centrifugal separation, thereby providing a separated serum phase which is completely free from latently formed fibrin and from suspended powdered means.

14. Apparatus for collecting whole blood and centrifugally separating the blood into a serum phase and a red cell phase comprising, vessel means for collecting a body of whole blood, gel-like means for establishing a barrier in a position between the separated serum and red cell phases, said gel-like means being thixotropic in nature and having a density between the densities of the serum and red cell phases, said gel-like means being disposed in an initial location in said vessel means and movable during centrifugation from said initial location in said position; means in said vessel means for directing said gel-like means from said initial location to said position between separated serum and red cell phases; and powder means within said vessel means for establishing blood clotting contact-activation sites throughout said body of collected blood, said powder means comprising a plurality of particles made from a clot-promoting material, said particles having a density greater than that of said serum phase and a size sufficient to allow both initial and extended suspension thereof within said body of blood as said body of blood is supplied to said vessel means, said particles having a minimum particle size capable of being precipitated from said serum phase during centrifugal separation of said blood into said phases; and said powder, through the establishment of activation sites throughout the blood, providing means for complete coagulation of the blood before the centrifugal separation thereof, with said minimum particle size providing means for complete precipitation of said powder during the centrifugal separation of the blood, thereby providing a separated serum phase which is completely free from latently formed fibrin and from suspended powder means.

15. The apparatus of claim 1 wherein said means for directing said gel-like means comprises a member having a density greater than said gel-like means and which applies a force to said gel-like means moving it away from its initial location during centrifugation.

* * * * *